United States Patent [19]

Pickering

[11] 4,003,378

[45] Jan. 18, 1977

[54] TRANSPORT AND LIFE-SUPPORT SYSTEM FOR INFANTS

[76] Inventor: Donald E. Pickering, 890 Mill St., Suite 400, Reno, Nev. 89502

[22] Filed: Oct. 18, 1974

[21] Appl. No.: 516,119

[52] U.S. Cl. .................. 128/204; 128/1 B; 128/30

[51] Int. Cl.$^2$ .................................A61M: 16/02

[58] Field of Search .............. 128/1 B, 28, 30, 30.2, 128/145.8, 191 A, 204, 145.5, 142, 142.8, 142.4, 191 R, 185, 298, 299, 202, 203

[56] References Cited

UNITED STATES PATENTS

| | | | |
|---|---|---|---|
| 2,776,657 | 1/1957 | Batson et al. | 128/1 B |
| 2,822,803 | 2/1958 | Huxley et al. | 128/30 |
| 3,000,379 | 9/1961 | Viers | 128/1 B |
| 3,335,713 | 8/1967 | Grosholtz et al. | 128/1 B |
| 3,783,863 | 1/1974 | Kliever | 128/134 |
| 3,786,809 | 1/1974 | Kitrilakis | 128/191 A |
| 3,889,670 | 6/1975 | Loveland et al. | 128/204 |

FOREIGN PATENTS OR APPLICATIONS

| | | | |
|---|---|---|---|
| 510,199 | 4/1952 | Belgium | 128/1 B |
| 194,163 | 8/1904 | Germany | 128/30 |

*Primary Examiner*—Robert W. Michell
*Assistant Examiner*—Henry J. Recla
*Attorney, Agent, or Firm*—Klarquist, Sparkman, Campbell, Leigh, Hall & Whinston

[57] ABSTRACT

A transport and life-support system for an infant with respiratory distress syndrome or other illness includes a semi-rigid tray having a detachable bumper and a rigid transparent life-support hood releasably attached to the tray and provided with ports for the introduction of air and oxygen into the hood and for the attachment of pressure regulating means thereto. The hood is adapted to receive the head and chest of the infant and is adhesively sealed to the chest with a reinforced plastic material.

14 Claims, 4 Drawing Figures

TRANSPORT AND LIFE-SUPPORT SYSTEM FOR INFANTS

BACKGROUND OF THE INVENTION

This invention relates to life-support systems for infants with respiratory distress syndrome and other illnesses and, more particularly, to a life-support system that facilitates transportation of the infant.

Prior life-support systems for infants which provide controlled atmospheric conditions have generally been sealed and attached at the infant's neck. Attaching and sealing of such apparatus at the neck tends to interfere with the flow of blood to the head and neck, interferes with the respiratory passages, and also tends to restrict head and neck motion. Such prior systems have also generally been made of flexible plastic material. A unit made of such material cannot protect an infant from physical injury.

Accordingly, it is the primary object of the present invention to provide a transportation and life-support system for an infant with respiratory distress syndrome or other illness, which system will enable maintenance of controlled atmosphere and ventilation requirements for the infant and will also adequately protect him from injury.

It is a further object of the present invention to provide such a system that will provide continuous delivery of air, oxygen or an air-oxygen mixture to the infant at controlled pressure, temperature, humidity and oxygen saturation and which will maintain such conditions both during in-house use as in hospital nurseries and during transportation of the infant by land, sea or air.

A further object of the present invention is to provide such a system which will enable maintenance of controlled atmosphere and ventilation for the infant either with or without the use of tracheal intubation.

A still further object of the present invention is to provide such a system which will not interfere with arterial or venous bloodflow to the head and neck of the infant, which will not interfere with respiratory passages and which will not restrict head or neck motion.

It is a still further object of the present invention to provide such a system that will insure adequate ventilative pressure in transportation for a child who may or may not need such ventilative support.

It is a still further object of the present invention to provide such a system that will attach and seal at the chest of the infant, yet will not constrict the chest.

It is a still further object of the present invention to provide such a system that will provide free access to the head and neck of the infant, will not restrict diaphragm action, and will not interfere with the infant's breathing.

It is a still further object of the present invention to provide such a system that will avoid interference with other equipment used to treat the infant, as, for example, with EKG monitoring or intravenous feeding apparatus.

It is a still further object of the present invention to provide such a system which will not adversely influence total chest volume during diaphragmatic breathing, which will maintain maximum chest circumference and which will actually aid diaphragmatic breathing.

It is a still further object of the present invention to provide such a system that will provide for quick installation and disassembly, yet which will adequately protect and shield the infant from physical traumatic injury.

SUMMARY OF THE INVENTION

My transport and life-support system comprises tray means having a semi-rigid bottom pad sized to accommodate an infant in prone position and rim means including a semi-rigid bumper releasably attached to the bottom pad adjacent the periphery thereof.

I further provide rigid transparent hood means releasably attached to the tray means adjacent one end thereof. Such hood means comprises a bottom, a rigid transparent top and a plurality of rigid transparent sides. The one such side of the hood means facing the other end of the tray means is provided with an opening therein, and such opening is adapted to receive the head and chest of an infant within the hood means.

I further provide means adhesively to seal the chest of the infant to the periphery of the opening, thus to create a gas tight enclosure about the head and chest. First port means are provided in the hood means for introducing air and oxygen into the hood means and second port means are provided for regulating the pressure of the air and oxygen within the hood means.

A large port is provided in the top of the hood means for obtaining access to the infant, and a removable sealable transparent cover is provided to close such access port. Preferably the bottom, top and sides of the hood means are made of rigid transparent plastic adequate in thickness to provide protection and shielding for the infant as during transportation thereof.

DESCRIPTION OF THE PREFERRED EMBODIMENT

Figure 1:
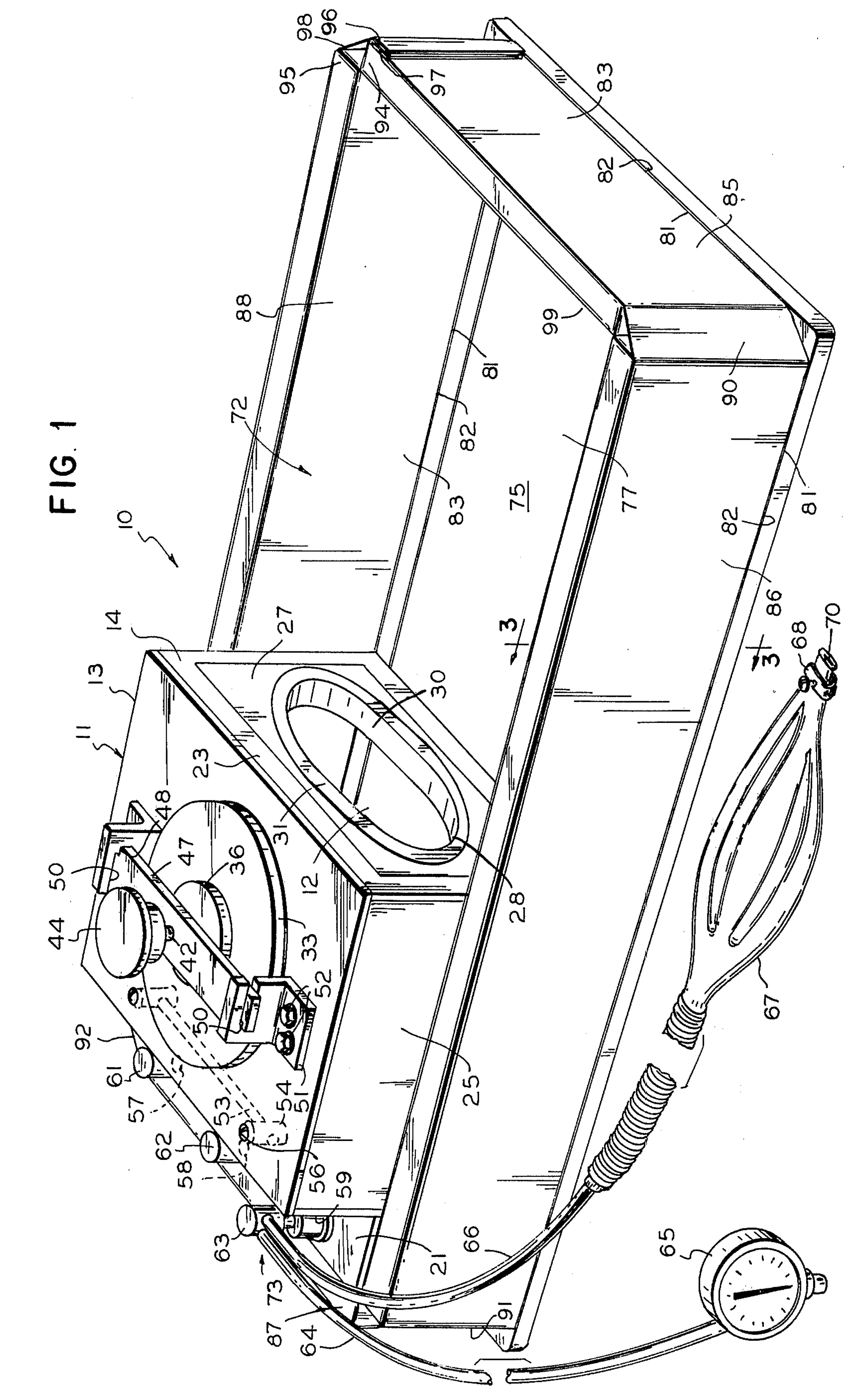
FIG. 1 is a perspective view of a transport and life-support system in accordance with the present invention.

As shown in the drawings, my transport and life-support system 10 comprises a rigid transparent hood 11 large enough to accommodate the head and upper torso to about the chest of an infant suffering from respiratory distress syndrome or other illness. As such, the hood 11 includes a bottom or base plate 12 and a smaller horizontal top plate 13, the forward edge 14 of which is in register with the forward edge 15 of the base plate 12. The back edge 16 of the base plate 12 is attached to a first or lower vertical back plate 17. The back edge 18 of the top plate 13 is attached to a second or upper vertical back plate 20. The two back plates 17 and 20 are joined by a horizontal adapter plate 21, thus to form a shoulder 22 for the hood. The forward edges 14 and 15 of the plates 13 and 12, respectively, are joined by a vertical front plate 23 having a large rectangular opening 24. Two side plates 25 and 26 complete the enclosure. All plates are preferably made of one-fourth inch thick acrylic, which is a rigid transparent plastic material.

The front plate 23 has a panel 27 of 30 mil unreinforced Silastic brand plastic attached about the opening 24, and the panel 27 is itself provided with an oval shaped opening 28 large enough to receive the head and chest of an infant within the hood 11 with the rest of the body of the infant extending outside. A sealing means comprising an L-shaped collar 30 preferably made of 20 mil polyester fiber reinforced Silastic brand plastic is provided for adhesive sealing attachment to the infant's chest, the upstanding leg 31 of the collar being similarly adhesively attached to the panel 27 after the infant has been placed within the hood, thereby to create a gas tight enclosure about the head and chest of the infant. An adhesive suitable for the purpose is Dow Corning medical B adhesive. Bonding of the collar 30 to the infant's chest with the adhesive does not constrict the chest nor interfere with normal breathing activity as would attachment by a pressure inducing means.

The top plate 13 is provided with an access opening or port 32 large enough for access to the infant's head and neck. The port 32 is illustrated as being circular in shape, but it may be oval or any other shape as long as it provides adequate access to the infant's head and neck when the infant is in the hood. A complementary shaped cover plate 33 of one-half inch Plexiglas plastic having an annular shoulder 34 and provided with a neoprene gasket 35 is receivable in the access port 32 to close and seal the same. A circular plate 36 having a recessed center 37 is attached to the cover plate 33 by screws 38 and is provided with a central opening 40 to receive the bearing end 41 of a threaded shoulder bolt 42, the other end 43 of which is threadedly engaged with an acrylic knob 44 and retained in position by a nut 45. An anodized aluminum washer 46 is positioned above the plate 36 also to receive the bolt 42, which is retained in the plate 36 by a snap ring **42*a***.

An anodized aluminum locking arm 47 having end notches 48 is threadedly received on the bolt 42 and is adapted to engage complementary slots 50 in anodized aluminum L-shaped locking brackets 51 mounted with bolts 52 on each side of the top plate 33, as shown. Clockwise rotation of the knob 44 causes the shoulder portion of the bolt 42 to bear downwardly on the washer 46 while causing the arm 47 to rise on the threaded portion of the bolt 42 and react against the top of the slots 50 in the brackets 51, thereby to force the gasket 35 in the shoulder 34 of the cover plate 33 into sealing engagement with the top plate 13.

A thermometer 53 is mounted in posts 54 attached to the under surface 55 of the top plate 13 by screws 56, as shown.

The adapter plate 21 is provided with three ports 57, 58 and 59, as shown. The first port 57 is provided with an adapter 61 for introduction of air, oxygen or mixtures thereof from a suitable source. The air and/or oxygen mixture is provided by standard apparatus providing humidification and heat to the gases as desired. The second port 58 is provided with an adapter 62 for connecting an oxygen pressure monitoring gauge or other similar equipment. The third port 59 serves as a means of regulating the pressure of air and oxygen within the hood. Port 59 as such is provided with a coupling 63 which serves as a hose attachment for a first hose 64 connected to a pressure gauge 65 and a second hose 66 connected to a pediatric rebreathing bag 67. An adjustable clamp 68 is provided at the end of the bag 67 to form an adjustable orifice 70, thereby to regulate the exhaust rate from and thus the pressure within the hood 11.

An infant requiring continuous positive airway pressure can thus be placed in the hood and sealed therein as hereinabove described. A suitable air-oxygen mixture is introduced through the port 57 and the clamp 68 is adjusted to regulate the pressure within the hood which is monitored by the gauge 65.

My transport and life-support system further comprises a tray 72 in which the hood 11 is placed adjacent one end 73. The hood 11 is desirably provided with Velcro attaching strips 74 along opposed edges of its base plate 12 for attachment to complementary Velcro strips on a semi-rigid bottom pad 75 of the tray 72.

Velcro is a brand of interlocking loop and pile fastening strips manufactured by Minnesota Mining and Manufacturing Corp.

The bottom pad 75 is made of one-half inch thick soft plastic foam 76 received in a plastic impregnated fabric cover 77 and supported by one-half inch diameter polyvinyl chloride tubing 78 at the periphery thereof.

The upper surface of the cover 77 is provided with additional Velcro attaching strips 80 at the periphery thereof for releasable attachment of the bottom pad 75 to mating Velcro attachment strips 81 attached to the lower edges 82 of a semi-rigid bumper 83. The bumper 83 is also made of soft plastic foam 89 received in a plastic impregnated fabric cover 84 and is desirably made in four sections 85, 86, 87 and 88 which correspond in size to the edge dimensions of the bottom pad 75. The four sections 85, 86, 87 and 88 are attached together by three sewn seams 90, 91 and 92. The ends 94, 95 of the bumper 83 are provided with vertically disposed mating Velcro attachment strips 96, 97 so that such ends can be joined together at one corner 98, as shown.

As can be seen from the drawings, the tray 72 is sized so that the hood 11 fits into the end 73 thereof, the hood 11 being positioned at such end 73 to permit the lower portion of the infant's body to extend outside the hood and into the other end 99 of the tray. The entire assemblage is sized to fit in an incubator or on the top of a standard medical cart 100 which may be provided with a slotted table top 101 to prevent the tray from lateral displacement. See FIG. 4.

Figures 2, 3, 4:
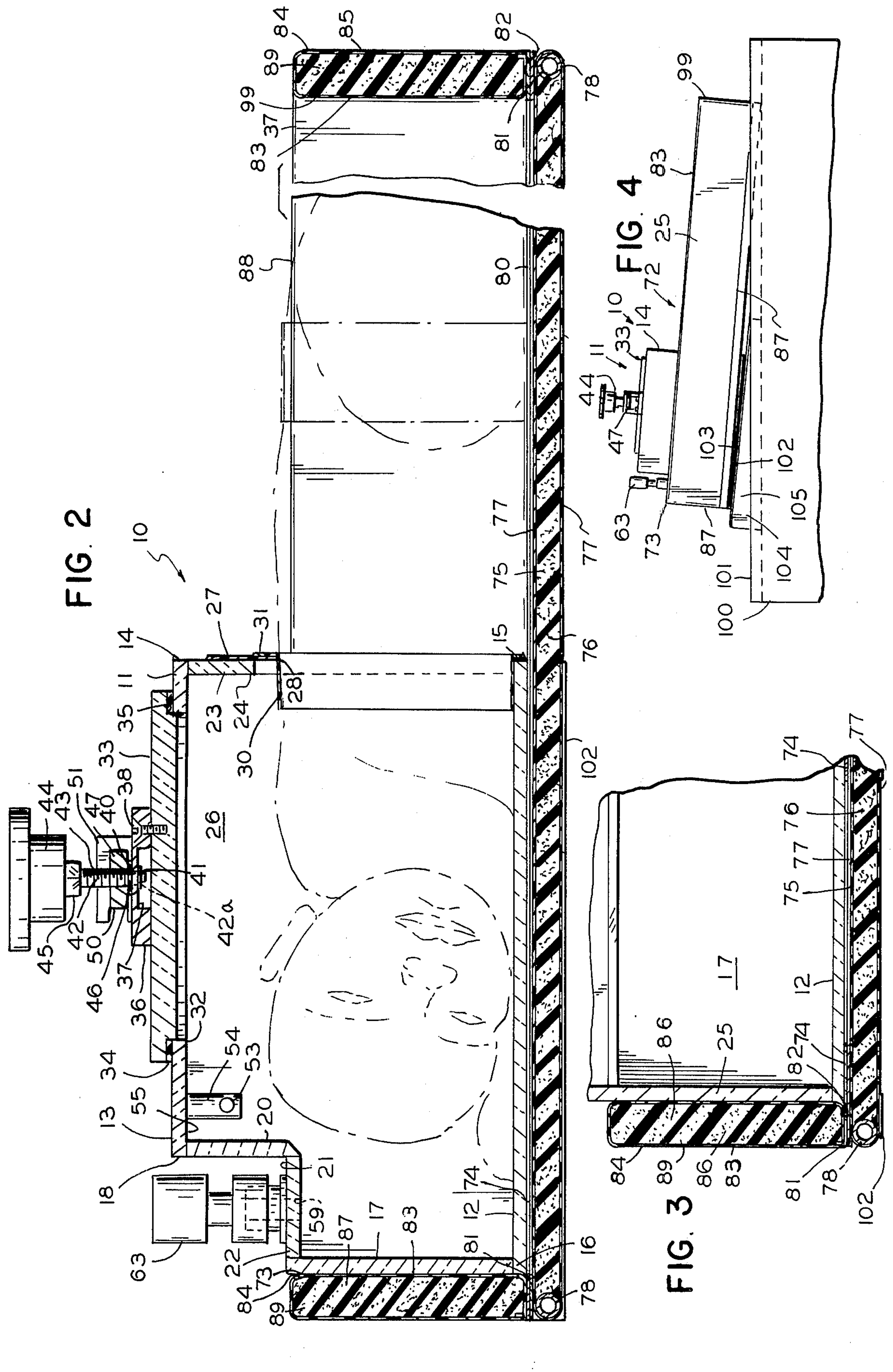
FIG. 2 is a longitudinal sectional view of the system of FIG. 1.
FIG. 3 is a partial sectional view taken on line 3—3 of FIG. 1.
FIG. 4 is a side elevational view of the system in position on a cabinet top and illustrating optional elevation of one end of the system by wedge means adapted to provide the system with a desired elevation or tilt.

The underside of the bottom pad 75 is provided with still additional Velcro attachment strips 102 for mating attachment to Velcro strips 103 secured to a semi-rigid wedge 104 also made of soft plastic foam received in a plastic impregnated fabric cover 105. As shown in FIG. 4, the wedge 104 may be placed under the end 73 of the tray to elevate such end, if desired. Optionally, the wedge may be placed under the other end 99 of the tray to tilt the infant in the opposite direction. The infant may also be tilted to the left or to the right by placing the wedge appropriately on either side of the tray.

Using Velcro attaching strips releasably to attach the semi-rigid bumper 83 to the bottom pad 75 permits rapid disassembly of the tray 72 and corresponding rapid access to the infant. The bumper 83 can be removed with the infant in place in the tray 72 merely by positive pulling action on any section 85, 86, 87, 88 thereof, however the Velcro attachment will retain the bumper 83 in place during normal operations.

It is thus seen that my transport and life-support system permits continuous delivery of air, oxygen or an air-oxygen misture to an infant under controlled pressure, temperature and humidity conditions and as such, is suitable either for in-house use in nurseries or during transportation of the infant by any means.

Sealing and attachment of the hood at the infant's chest rather than at his neck as in prior units eliminates any possible interference with arterial or venous blood-flow to the head or neck, eliminates interference with respiratory passages and places no restrictions on head or neck motion. The rigid construction of the hood protects and shields the infant from physical traumatic injury.

Attachment of the hood by adhesive sealing to the infant's chest rather than by pressure means avoids constricting the chest and does not adversely influence total chest volume during diaphragmatic breathing. The opening 28 in the Silastic plastic panel 27 maintains maximum chest circumference and the apparatus thus acts as an aid to diaphragmatic breathing. The Silastic material is capable of being sterilized and being an inert material, can not adversely affect the infant.

Bonding the hood to the infant's chest provides free access through the port 32 to the head and neck regions. The size and rigid nature of the hood 11 make it possible to operate either with or without a tracheal tube. The pressure system makes possible positive pressure and atmosphere control without the necessity of a tracheal tube and the hood 11 eliminates the necessity for a tracheal tube in administering oxygen and/or air under pressure when the infant suffers from respiratory distress syndrome. The hood 11 also insures adequate ventilative pressure during transportation of an infant who may or may not need ventilative support, again without the necessity of a tracheal tube.

The system does not interfere with other equipment used to treat the infant, as for example, EKG monitoring apparatus which may be attached to the infant's chest, and also permits umbilical artery catherization for intra-arterial infusion.

Attachment of the hood 11 to the tray 72 with Velcro attachment strips prevents the hood from bouncing and displacement with respect to the tray as might occur during air transportation of the infant.

Normally, when an infant is being transported by air, sealing means will be employed such that the pressure within the hood is maintained equivalent to that at which the infant originally was placed in the device. If, however, an infant does not require continuous positive airway pressure within the hood, but is able to function at normal atmospheric pressure, a seal will not be used, thereby to obviate the necessity for use of the rebreathing bag 67 and pressure gauge 65.

The system is designed for compatible use with standard air-oxygen mixing apparatus and the usual humidification and warming devices which are placed in-line on the supply system. Such standard air-oxygen supply apparatus provides for varying percentages of air and oxygen under standard pressures which can be adjusted for supplying the system as the physician desires.

I claim:

1. A life-support hood for an infant comprising:

a bottom;

a rigid transparent top;

a plurality of rigid transparent sides, one of said sides being provided with a body entrance opening therein, said opening being adapted to receive the head, shoulders, arms and chest of an infant within said hood with the rest of the body of said infant extending outside said hood;

sealing means within said opening for adhesively attaching and sealing said chest of said infant to said one side of said hood to selectively create a gas-tight enclosure;

a first port for introducing air and oxygen into said hood; and a second port for regulating the pressure of said air and oxygen within said hood, such that the gas pressure within said hood can be maintained at levels above ambient atmospheric pressure for providing continuous positive airway pressure in said infant.

2. A life-support hood for an infant comprising:

a bottom;

a rigid transparent top;

a plurality of rigid transparent sides, one of said sides being provided with a body entrance opening therein, said opening being adapted to receive the head, shoulders, arms and chest of an infant within said hood with the rest of the body of said infant extending outside said hood;

sealing means within said opening for adhesively attaching and sealing said chest of said infant to said one side of said hood to selectively create a gas-tight enclosure;

a first port for introducing air and oxygen into said hood;

a second port for regulating the pressure of said air and oxygen within said hood, such that the gas pressure within said hood can be maintained at levels above ambient atmospheric pressure for providing continuous positive airway pressure in said infant;

and a variable orifice means attached to said second port for regulating the rate of exhaust from said hood and a pressure gauge in communication with the interior of said hood for measuring the atmospheric pressure therein.

3. The hood of claim 2 further comprising an access port in said top of said hood for obtaining access to said infant.

4. The hood of claim 3 further comprising a rigid transparent cover for said access port, said cover being adapted to make a gas tight seal with said top.

5. The hood of claim 2 in which said sealing means comprise a flexible plastic panel attached to said one side about said opening therein, said panel having a second opening therein to receive said head and chest of said infant, and a flexible plastic collar having two legs, one said leg of said collar being adapted to be adhesively sealed to said chest of said infant, the other said leg of said collar being adhesively sealed to said panel about said second opening therein.

6. The hood of claim 5 in which said second opening in said plastic panel comprises an oval shaped opening.

7. The hood of claim 1 in which said bottom, said sides and said top of said hood means comprise rigid transparent plastic material.

8. A transport and life-support system for infants comprising tray means comprising a semi-rigid bottom pad sized to accommodate an infant in prone position, and rim means comprising a semi-rigid bumper releasably attached to said bottom pad adjacent the periphery thereof; and rigid transparent hood means releasably attached to said bottom pad adjacent one end thereof, said hood means comprising a bottom, a rigid transparent top, and a plurality of rigid transparent sides, one of said sides of said hood means facing the other end of said tray means, said one side being provided with an opening therein, said opening being adapted to receive the head and chest of said infant within said hood means, means adhesively to seal said chest of said infant to the periphery of said opening to create a gas tight enclosure about said head and chest of said infant, first port means in said hood means for introducing air and oxygen into said hood means, and second port means in said hood means for regulating the pressure of said air and oxygen within said hood means.

9. The system of claim 8 in which said bottom pad comprises a plastic foam pad and a plastic impregnated fabric cover, said plastic foam pad being received in said cover.

10. The system of claim 8 in which said rim means comprises a plastic foam bumper and a plastic impregnated fabric cover, said plastic foam bumper being received in said cover.

11. The system of claim 8 in which said bumper is releasably attached to said bottom pad by mating interlocking loop and pile fastening strips.

12. The system of claim 8 in which said hood means is releasably attached to said bottom pad by mating interlocking loop and pile fastening strips.

13. The system of claim 8 further comprising a semirigid wedge for placement under a desired end of said tray means.

14. A portable life-support chamber for the intensive care of an infant comprising:

rigid wall means defining an enclosure for at least the head and chest portions of an infant, said enclosure defining an interior chamber space extending uninterrupted from the top of an infant's head to at least the infant's chest so as not to confine the infant in the body regions between such body points, said rigid wall means including at least a top wall portion of transparent material;

access means providing access to the interior of said enclosure for placement of an infant therein and treatment of said infant, sealing means in conjunction with said access means for providing selectively a gas-tight said enclosure, means for introducing air and oxygen into said enclosure, and means for elevating the pressure of the atmosphere within said enclosure above ambient air pressure for providing continuous positive airway pressure, said means for elevating the pressure of the atmosphere within said enclosure comprising a pediatric rebreathing bag including a variable orifice means attached to an exhaust port of said enclosure for regulating the rate of exhaust from the enclosure and a pressure gauge in communication with the interior of said enclosure for monitoring the atmospheric pressure therein.

* * * * *